United States Patent [19]

Hope

[11] Patent Number: Plant 5,592

[45] Date of Patent: Dec. 10, 1985

[54] IMPATIENS PLANT NAMED VISTA IMPATIENS NO. 13

[75] Inventor: Claude Hope, Cartago, Costa Rica

[73] Assignee: Pan American Plant Company, Parrish, Fla.

[21] Appl. No.: 566,802

[22] Filed: Dec. 29, 1983

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of impatiens plant named Vista Impatiens No. 13 characterized by its very large vivid orange-red flowers, dark attractive green foliage, good keeping qualities, and by its compact and dense self-branching habit, making the new cultivar ideal for bedding plants, pot plant culture and hanging baskets.

1 Drawing Figure

1

The present invention relates to a new and distinctive cultivar of impatiens plant, botanically known as Impatiens, and known by the cultivar name Vista Impatiens No. 13. The new cultivar was developed by me from a planned program of hybridization to obtain impatiens plants having a wide range of colors and with very large flowers derived from the New Guinea complex of species collected by the Longwood Garden Expedition of 1970. The new cultivar was identified during the breeding and selection process by seedling No. 3342-30-5, and resulted from the cross breeding of seedling No. 3018-22 (from Impatiens Mooreana P.I. 366030)×3342-1, a seedling of unknown origin.

The new cultivar was selected in 1981, and asexual reproduction by terminal or stem cuttings taken at Cartago, Costa Rica has shown that the unique features of this new impatiens are stabilized and reproduced true to type in successive propagations.

The following characteristics distinguish the new impatiens from both its parent varieties and other cultivated impatiens of this type known and used in the floriculture industry:

1. Vista Impatiens No. 13 was selected and is principally characterized by its very large flower size and vivid orange-red flower color, dark green foliage, compact and dense habit, and profuse blooming.
2. Flowers are very large (75 mm.) and are vivid orange-red in color with a lighter colored eye. The flowers are the largest produced in the planned breeding program.
3. Foliage is dark green in color and provides a striking contrast with the flower color.
4. Habit is compact and dense (35–45 cm. when full grown), making it ideal for hanging baskets, pot plant culture and bedding plants.
5. Good keeping qualities when grown outdoors in full sun (fall, winter and spring) and under light shade (summer) in Florida.
6. Growth rate is moderate, producing in 6–8 weeks a saleable plant 20–30 cm. tall and 30 cm. in diameter.
7. Flowers last for several days under optimal conditions (80° F.days — 60° F. nights).
8. Excellent self-branching habit is exhibited.

The accompanying colored photograph illustrates overall appearance of this cultivar, showing the colors true as it is reasonably possible to obtain in a colored reproduction of this type.

2

The following is a detailed description of my new impatiens cultivar based on plants produced under commercial practice in Cortez and Parrish, Fla. The plants were grown outdoors in full sun during winter, spring and fall months, and under light shade in Cortez, Fla. during the summer months. Color references are made to The Royal Horticultural Society Colour Chart except where general terms of ordinary dictionary significance are used.

Parentage:

A. *Time cutting.*—Tip cuttings with stems of 5 cm.

B. *Time to initiate roots.*—10–14 days at 27° C. summer; 12–16 days at 18° C. winter.

C. *Rooting habit.*—Abundant and fibrous.

Plant description:

A. *Form.*—Compact, dense, self-branching, spreading, low dome-shaped.

B. *Habit of growth.*—Rate of growth moderate for this type of plant; vegetative shoots are formed at lower nodes and flowers at the higher nodes.

C. *Foliage description.*—Lower leaves opposite, higher leaves in whorls of 4–7. Leaves are simple.

(1) *Size.*—Average full grown leave is 153 mm. long×50 mm. wide. Full grown leaves attached to petioles 47 mm. long. Young leaves have 2–5 mm. long petioles.

(2) *Shape.*—Elliptic; apex acuminate, base attentuate.

(3) *Texture.*—Smooth; glabrous.

(4) *Margin.*—Serrulate.

(5) *Color.*—Young foliage, top side green 137A-B, under side greyed green 191B; mature foliage, top side green 147A, under side greyed green 191B.

(6) *Venation.*—Pinnate; main vein yellow green 145C.

Flowering description:

A. *Flowering habits.*—Very floriferous, flowers occurring progressively around the whorl of leaves. Flowers are large and single.

B. *Natural flowering season.*—Flowering is indeterminate and occurs throughout the year except for periods of high light and high temperature in Florida.

C. *Flower bud description.*—Conical, covered with 3 sepals; upper two sepals are 12 mm. long×7 mm. Apex acuminate. Lower sepal 15 mm. long×7 mm. wide, apex acuminate. Upper sepals are green and lower sepal is colorless infused with green. Hollow spur, 28 mm. long on bud, 32 mm. long on open flower, connected to lower sepal. Spur is a light green in color.

D. *Flowers borne.*—On peduncles, 61 mm long, green in color.

E. *Quantity of flowers.*—One flower per leaf, occurring progressively around the whorl of leaves.

F. *Petals.*—Top petal heart-shaped with a wide rounded base (no point). All other petals are heart-shaped. Occasionally petals are heart-shaped with a lobe (small) where petal curves to form the heart-shape.

(1) *Color.*—Top side, orange red 33A when opening wih a lighter to whitish colored eye, fading to red 40B; under side close to and between red 43C and D.

(2) *Number of petals.*—Five.

(3) *Size of flowers.*—Top petal 35 mm. long×40 mm. wide; 2 middle petals 37 mm. long×27 mm. wide; 2 bottom petals 40 mm. long×29 mm. wide. Total flower diameter is 75 mm.

G. *Reproductive organs.*—(1) Stamens: Five in number, with the lower stamen being shorter than the other stamens. Stamens united in an asymmetrical tube surrounding and covering the ovary. (a) Anther shape; Hooded, colorless to cream. (b) Pollen color: Cream. (2) Pistils: (a) Stigma shape: Five-pointed star, colorless (b) Styles: Very short, cream in color. (c) Ovaries: 5 celled ovary, 6 mm., green.

Disease resistance:

No general plant diseases noted. Insect problems can include the two spotted spider mite which can cause foliar injury and thrips which can cause stunting and injury of the growing tip.

I claim:

1. A new and distinct cultivar of impatiens plant named Vista Impatiens No. 13, as described and illustrated, and characterized by its very large vivid orange-red flowers, dark green attractive foliage, good keeping qualities, and by its compact and dense self-branching habit, making the new cultivar ideal for bedding plants, pot plant culture and hanging baskets.

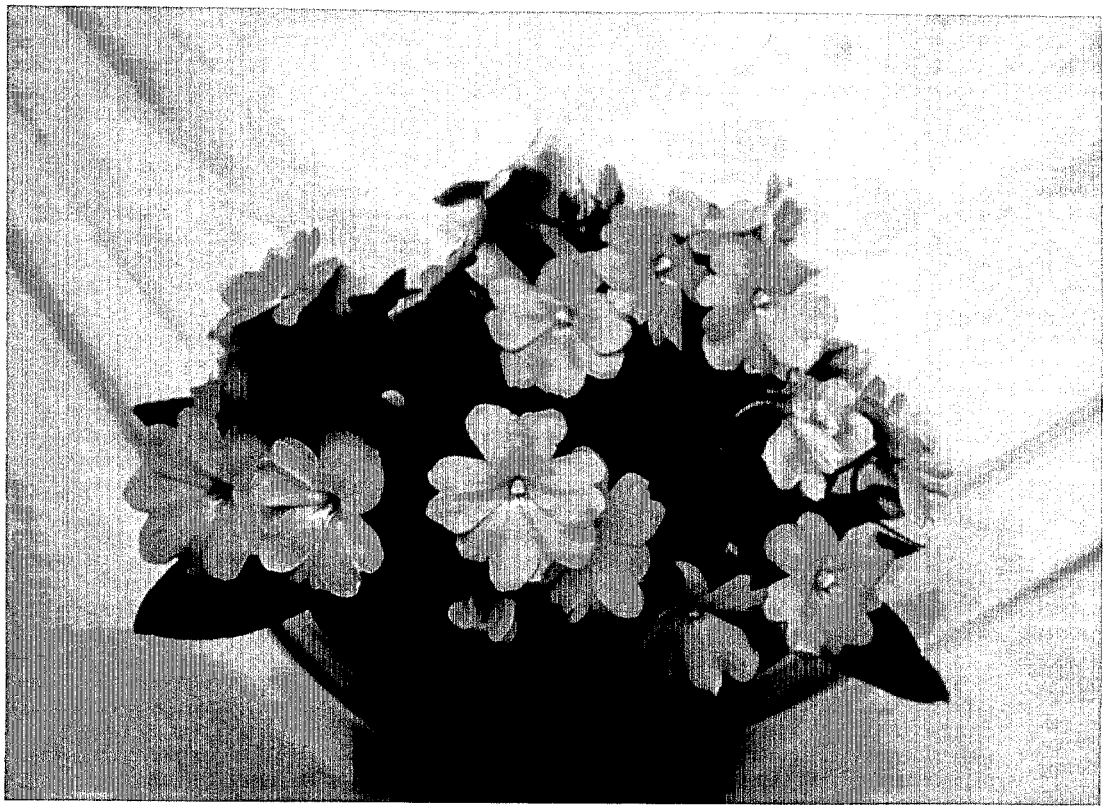

* * * * *